US008486238B2

(12) United States Patent
Park et al.

(10) Patent No.: US 8,486,238 B2
(45) Date of Patent: Jul. 16, 2013

(54) SURFACE RENEWABLE IRIDIUM OXIDE-GLASS OR CERAMIC COMPOSITE HYDROGEN ION ELECTRODE (75) Inventors: Jong Man Park, Gyeonggido (KR); Ji Young Kim, Seoul (KR)

(73) Assignee: Konkuk University Industrial Cooperation Corp., Seoul (KR)

(*) Notice: Subject to any disclaimer, the term of this patent is extended or adjusted under 35 U.S.C. 154(b) by 357 days.

(21) Appl. No.: 12/846,791

(22) Filed: Jul. 29, 2010

(65) Prior Publication Data

US 2011/0031114 A1 Feb. 10, 2011

Related U.S. Application Data (63) Continuation-in-part of application No. 11/764,906, filed on Jun. 19, 2007, now abandoned.

(30) Foreign Application Priority Data

Jun. 23, 2006 (KR) .................. 10-2006-0056722

(51) Int. Cl.
*C25B 11/04* (2006.01)
*H01B 1/02* (2006.01)

(52) U.S. Cl.
USPC ............. 204/280; 204/290.01; 204/290.14; 204/291; 428/426; 428/697; 428/702; 252/518.1; 252/520.3

(58) Field of Classification Search
None
See application file for complete search history.

(56) References Cited

U.S. PATENT DOCUMENTS

| 3,859,128 | A | * | 1/1975 | Burks et al. | ............... | 428/426 |
| 3,929,491 | A | | 12/1975 | Smith et al. | | |
| 4,187,155 | A | * | 2/1980 | de Nora et al. | ............... | 205/383 |
| 4,246,095 | A | | 1/1981 | Antos et al. | | |
| 4,302,321 | A | * | 11/1981 | deNora et al. | ............... | 204/291 |
| 4,944,985 | A | | 7/1990 | Alexander et al. | | |
| 5,942,676 | A | | 8/1999 | Potthast et al. | | |
| 6,162,334 | A | * | 12/2000 | Ray et al. | ............... | 204/290.14 |
| 6,423,195 | B1 | * | 7/2002 | Ray et al. | ............... | 204/291 |
| 2008/0229731 | A1 | | 9/2008 | Kikuhara et al. | | |

FOREIGN PATENT DOCUMENTS

JP 2003-486612 A * 3/2003

OTHER PUBLICATIONS

Hongmei Quan et al., Suface Renewable Hydrogen Ion-Selective Polymeric Composite Electrode Containing Iridium Oxide, Bull. Korean Chem. Soc., 2005, p. 156-1568, vol. 26, No. 10.
Derek Midgley, A Review of pH Measurement at High Temperatures, Talamta, 1990, p. 767-781, vol. 37, No. 8, Pergamon Press, Great Britain.
Paulus VanHoudt et al., Iridium Oxide pH Microelectrode, Biotechnology and Bioengineering, 1992, p. 601-608, vol. 40, John Wiley & Sons, Inc.
A. Fog. R. P. Buck, Sensors and Actuators, 1984, 5, 137-146.

* cited by examiner

*Primary Examiner* — David Sample
(74) *Attorney, Agent, or Firm* — Rabin & Berdo, P.C.

(57) ABSTRACT

Disclosed herein is a surface renewable iridium oxide-glass or ceramic composite hydrogen ion electrode and, more particularly, a surface renewable iridium oxide-glass or ceramic composite hydrogen ion electrode, which has a long life due to its excellent physical strength, pH dependency approximate to a theoretical value (59 mV/pH unit), and high surface renewability, and a method of manufacturing the same. The iridium oxide composite hydrogen ion electrode according to the present invention is effective in that, when the electrode is contaminated or inactivated, the surface of the electrode can be regenerated through a simple grinding process because the electrode has high surface renewability, unlike conventional electrodes. The iridium oxide composite electrode according to the present invention can be usefully used in a water-quality monitoring system for monitoring the hydrogen ion concentration of a solution for a long period, an online pH measurement system, and pH measurement for samples, which causes serious contamination of the surface of a sensor.

8 Claims, 7 Drawing Sheets

SURFACE RENEWABLE IRIDIUM OXIDE-GLASS OR CERAMIC COMPOSITE HYDROGEN ION ELECTRODE

CROSS-REFERENCE TO RELATED APPLICATIONS

This is a Continuation-in-part Application of U.S. application Ser. No. 11/764,906, filed on Jun. 19, 2007, which claims the benefit of priority from Korean Patent Application No. 10-2006-0056722, filed on Jun. 23, 2006, the disclosures of both of which are expressly incorporated by reference herein in their entireties.

BACKGROUND OF THE INVENTION

1. Field of the Invention

The present invention relates to a surface renewable hydrogen ion electrode made of iridium oxide-glass or ceramic composite materials, and, more particularly, to a surface renewable iridium oxide-glass or ceramic composite hydrogen ion electrode, which has long lifetime due to its excellent physical strength, pH dependency approximate to the theoretical value (59 mV/pH unit), and high surface renewability, and to a method of manufacturing the same.

2. Description of the Related Art

Generally, pH is one of basic analytical parameter measured in various fields, such as environmental, nutritional, medical, medicinal, physiological, or chemical fields. In particular, pH glass membrane electrodes have been used generally in the case where electrodes are exposed to the possibilities of contamination due to prolonged exposure, as in a long-term water-quality monitoring system, or in the case where pH is measured in harsh environments causing contamination of the surface of the sensor, like samples used in soil analysis processes, food production processes and the like. However, the pH glass membrane electrodes are fragile, so they can be broken easily. They have to be changed or reactivated periodically whenever they are contaminated or fouled due to the long-period exposure of the sensors to environmental samples. However, it is hardly to find any effective method for overcoming the inactivation and fouling problems.

Polymer membrane ion selective electrodes or coated-wire type selective electrodes, based on ionophores or ion carriers, are advantageous in that they are easily manufactured and can be miniaturized in a small size. But they are disadvantageous in that, since they are formed of a physically weak and thin polymer film. They can be easily torn and it is impossible to reactivate and regenerate the surface thereof.

Meanwhile, it was reported in the document (A. Fog, R. P. Buck, *Sensors and Actuators*, 1984, 5, 137-146) that metal oxide films formed on the surface of precious metal electrodes can be used for measuring hydrogen ion concentration because the electrode potentials due to the oxidation-reduction reaction of the metal oxides are dependent on the hydrogen ion concentration, and these metal oxides include $TiO_2$, $RuO_2$, $RhO_2$, $SnO_2$, $Ta_2O_5$, $OsO_2$, $PdO_2$, $PtO_2$, $IrO_2$, and the like. The hydrogen ion selective electrodes using metal oxides are mostly based on the fact that the potentials due to the reversible oxidation-reduction reactions of the metal oxides are dependent on the hydrogen ion concentration. These metal oxide film based pH electrodes are manufactured using a sputtering method, a pyrolysis method, or an electrochemical oxidation method on metal foils or wires. As the result of basic electrochemical research, it was found that, among these metal oxides, iridium oxide ($IrO_2$) exhibits the most excellent hydrogen ion selectivity and sensitivity.

A typical electrochemical oxidation method is a method of dipping iridium (Ir) electrodes in a sulfuric acid solution and oxidizing iridium of the electrodes to iridium oxides by cycling the potential of the electrode in the range of −0.25 to +1.25 V (vs. SCE). The iridium oxides formed on the metal electrodes are hydrated iridium oxides, such as $IrO_2.4H_2O$, $Ir(OH)_4.2H_2O$, $[IrO_2(OH)_2.2H_2O]^{2-}$, or the like. It is disclosed in the document (D. Midgly, *Talanta*, 1990, 37, 767-781) that the iridium oxides exhibit super-Nerntian response of about 90 mV/pH unit according to Equation 1 below.

[Equation 1]

Further, in the case of iridium oxide film electrodes formed on the surface of platinum or iridium electrodes using a sputtering method or a pyrolysis method. The iridium oxides formed on the electrodes are anhydrous iridium oxides, and exhibit responses of about 59 mV/pH unit according to Equation 2 or 3 below. It is disclosed in the document (P. Van-Houdt, Z. Lewandowski, B. Little, *Biotech. Bioeng.* 1992, 40, 601-608).

[Equation 2]

or

[Equation 3]

Recently, novel hydrogen ion electrodes having hydrogen ion sensitivity, durability and surface renewability were developed by combining the characteristics of above iridium oxide film hydrogen ion electrodes, having durability and hydrogen ion concentration dependency, with technologies for manufacturing carbon-polymer composite electrodes (H. Quan, W. Kim, K.-C. Chung, J. Park, *Bull. Korean Chem. Soc.* 2005, 26, 1565-1568).

The iridium oxide/carbon-polymer composite hydrogen ion electrodes have an advantage in that the medium thereof is composed of polymer materials and carbon black particles or graphite particles, which are conductors, and uniformly includes iridium oxide particles, exhibiting selective sensitivity to hydrogen ion, so that the electrodes have hydrogen ion selectivity and physical stability due to the mechanical strength of the polymers, thereby easily obtaining a renewable electrode surface through a simple polishing process, whenever the electrodes are inactivated and contaminated.

However, the iridium oxide/carbon-polymer composite pH electrodes have problems in that, although the electrodes have improved physical stability and surface renewability compared to conventional glass electrodes or polymer film electrodes, the manufacturing method of the electrode is complicated, the pH dependency of the electrodes varies greatly depending on the electrodes, and hysteresis occurs during repeated use of the electrodes. Moreover, the iridium oxide/carbon-polymer composite pH electrodes have a problem in that surface sensing materials can be worn out easily due to the low hardness of the polymeric media at the time of surface grinding and polishing for surface regeneration.

SUMMARY OF THE INVENTION

Accordingly, the present invention has been made to overcome the above problems occurring in the prior art, and an object of the present invention is to provide a surface renewable iridium oxide-glass or ceramic composite hydrogen ion electrode which has improved durability and surface renewability as well as response characteristics.

Another object of the present invention is to provide a method of manufacturing a surface renewable iridium oxide-glass or ceramic composite hydrogen ion electrode which has high durability and surface renewability.

In order to accomplish the above objects, an aspect of the present invention provides a surface renewable iridium oxide-glass or ceramic composite hydrogen ion electrode, which has a long lifetime due to its excellent physical and mechanical strength, has pH dependency approximate to the theoretical value (59 mV/pH unit), and maintains high surface renewability, which is an advantage of a metal oxide polymer composite pH electrode.

Another aspect of the present invention provides a method of manufacturing a surface renewable iridium oxide-glass or ceramic composite hydrogen ion electrode, including a first step of forming an inactive conductive material on a surface of high-temperature sinterable glass fine powder, ceramic powder or ceramic precursor powder; a second step of preparing high-temperature sinterable glass fine powder, ceramic powder or ceramic precursor powder, including metal/iridium oxides or iridium oxides alone, by dispersing the high-temperature sinterable glass fine powder, ceramic powder or ceramic precursor powder, coating on the surface thereof with the inactive conductive material formed in the first step or high-temperature sinterable glass fine powder, ceramic powder or ceramic precursor powder in a solution of iridium containing compound, evaporating and drying the solvent in the solution and thus applying the iridium compound on the surface of glass fine powder, ceramic powder or ceramic precursor powder, and then pyrolyzing compounds at below the sintering temperature; and a third step of molding the high-temperature sinterable glass fine powder, ceramic powder or ceramic precursor powder including metal/iridium oxides or iridium oxides alone and then high-temperature sintering or high-temperature high-pressure sintering the molded glass fine powder, ceramic powder or ceramic precursor powder.

In the first step, the inactive conductive material is selected from the group consisting of platinum (Pt), iridium (Ir), palladium (Pd), and gold (Au).

Further, in the first step, the inactive conductive material is formed using a reductive pyrolysis method, a simple mixing method, or an electroless plating method.

In the second step, it is preferred that the pyrolysis temperature of the applied compounds be in the range of 200 to 700° C.

Further, in the third step, the glass fine powder, ceramic powder or material powder, further including a binder, may be pressure-molded. In this case, preferably, the binder may be a polymer wax binder, but is not limited thereto.

Further, in the third step, preferably, the sintering temperature is in the range of 400 to 1,000° C., and more preferably 600 to 800° C. It is preferred that the sintering time be in the range of 3 to 5 hours.

Specifically, the first step is a step of being performed to maintain suitable electrical conductivity of the iridium oxide composite hydrogen ion electrode material prepared through the present invention. The first step can be omitted when iridium oxide, which is a sensing material, is used alone, because the electrical conductivity of the iridium oxide composite hydrogen ion electrode material, which is the final product, can be maintained with only iridium oxide.

In the first step, iridium compounds are dissolved in water, an organic solvent, or a mixture thereof. The organic solvent is not particularly limited, as long as it can dissolve iridium compounds.

Further, in order to improve the solubility of the iridium compound, an appropriate amount of acid may be added, or the components of the organic solvent may be changed.

The second step is a step of forming iridium oxides on the surface of the glass fine particles, ceramic particles or ceramic precursor powder. In the second step, iridium compounds are applied on the surface of high-temperature sinterable glass fine powder, ceramic particles or ceramic precursor powder having a size of 45 µm or less, or on the surface of the high-temperature sinterable glass fine powder, ceramic particles or ceramic precursor powder containing iridium metal particles, which is an inactive conductive material prepared in the first step, and the iridium oxides applied thereon are pyrolyzed in an oxygen or air atmosphere, thereby preparing glass fine powder, ceramic particles or ceramic precursor powder coated with the iridium oxide ($IrO_2$).

The third step is a step of preparing electrode materials. In the third step, the high-temperature sinterable conductive mixture of iridium oxide/glass fine powder, iridium oxide/ceramic particles or iridium oxide/ceramic precursor powder prepared in the second step, or a mixture of iridium metal/iridium oxide/glass fine powder, iridium metal/iridium oxide/ceramic particles or iridium metal/iridium oxide/ceramic precursor powder is molded or is molded while mixing a binder, and then the molded mixture is sintered at a temperature of 400 to 1,000° C. for 3 to 5 hours, thereby preparing an iridium oxide/glass or iridium oxide/ceramic composite pH electrode material or an iridium/iridium oxide/glass or iridium/iridium oxide/ceramic composite pH electrode material.

BRIEF DESCRIPTION OF THE DRAWINGS

The above and other objects, features and advantages of the present invention will be more clearly understood from the following detailed description, taken in conjunction with the accompanying drawings, in which.

DESCRIPTION OF THE PREFERRED EMBODIMENTS

Figure 1:
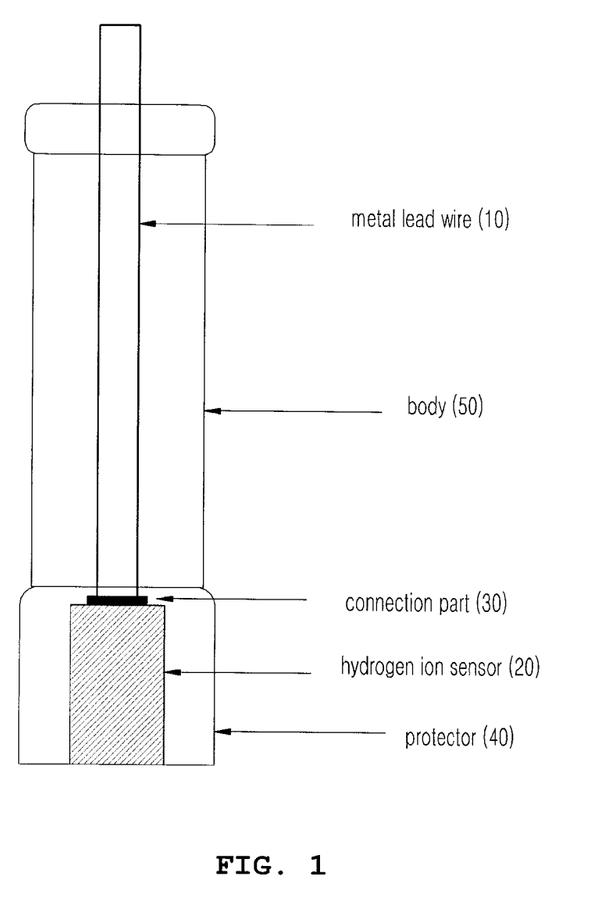
FIG. 1 is a view showing a structure of a hydrogen ion electrode according to an embodiment of the present invention.

First, FIG. 1 shows a structure of a hydrogen ion electrode according to an embodiment of the present invention.

As shown in FIG. 1, the hydrogen ion electrode according to an embodiment of the present invention includes: metal lead wire 10 connectable to a circuit unit for measuring potential change attributable to pH change; a surface renewable hydrogen ion sensor 20 including an iridium oxide composite material; and a connection part 30 for connecting the metal wiring and the hydrogen ion sensor.

The hydrogen ion electrode may further include: a protector 40 for protecting the hydrogen ion sensor 20 and the connection part 30; and a body 50 for protecting the metal wiring 10.

The connection part 30 may be made of silver epoxy.

Further, the protector 40 may be made of epoxy or plastic.

Moreover, the body 50 may be made of glass or plastic.

The hydrogen ion sensor 20 serves to detect the pH change of a sample to be measured, and may be formed in the shape of a pellet having a length of 0.5 mm or more. Since the hydrogen ion sensor 20 is formed in the shape of a pellet having the above length, the hydrogen ion sensor 20 can be renewed by grinding the surface of the hydrogen ion sensor using emery paper or SiC paper. The emery paper or SiC paper is only a tool used to grind the surface of the hydrogen ion sensor 20, and the surface of the hydrogen ion sensor 20 may be grinded using various tools in addition to the emery paper or SiC paper. Since the hydrogen ion sensor can be easily renewed by grinding the surface thereof, the hydrogen sensor can be repetitively and conveniently used until all the iridium oxide composite sensing material is exhausted, and thus it is possible to allow users to reduce the efforts and costs for maintenance and operation.

Hereinafter, a method of forming the hydrogen ion sensor 20 having a pellet shape will be described in more detail.

Here, these Examples are set forth to illustrate the present invention, but should not be construed as the limit of the present invention.

Example 1

Formation of Inactive Conductive Material 0.5 g of $(NH_4)_2IrCl_6$ was put in a 200 ml round bottomed flask, and was then dissolved in water by adding 50 ml of water to the flask. Subsequently, 5 ml of ethanol was additionally added to the solution in order to improve the solubility thereof.

Subsequently, 1.7 g of glass fine powder, having a particle size of 45 μm or less, was added to the flask, and the flask, to which the glass fine powder was added, was installed in a rotary evaporator, and then the solvent present in the flask was evaporated and dried at a temperature of 80° C., thereby coating the glass fine powder with $(NH_4)_2IrCl_6$.

Subsequently, the glass powder, coated with $(NH_4)_2IrCl_6$, was charged in a boat type crucible, and the crucible, containing the glass powder coated with the $(NH_4)_2IrCl_6$, was installed in a tubular furnace, and then the crucible was heated to a temperature of 500° C. for 5 hours in a hydrogen atmosphere, and thus the $(NH_4)_2IrCl_6$ applied on the surface of the glass powder was decomposed and reduced, thereby forming fine iridium metal particles on the surface of glass.

Example 2

Formation of Iridium Oxide 0.5 g of $(NH_4)_2IrCl_6$ was put in a 200 ml flask with a round bottom, and was then dissolved in water by adding 50 ml of water to the flask. Subsequently, 5 ml of ethanol was additionally added to the solution in order to improve the solubility thereof.

Subsequently, 1.7 g of glass fine powder having a particle size of 45 μm or less, or glass fine powder including iridium metal fine particles formed in Example 1, was added to the flask, and the flask, to which the glass fine powder was added, was installed in a rotary evaporator, and then the solvent present in the flask was evaporated and dried at a temperature of 80° C., thereby coating the glass fine powder with $(NH_4)_2IrCl_6$.

Subsequently, the glass powder, coated with $(NH_4)_2IrCl_6$, was charged in a boat type crucible, and the crucible, containing the glass powder coated with the $(NH_4)_2IrCl_6$, was installed in a tubular furnace, and then the crucible was heated to a temperature of 500° C. for 5 hours in an air or oxygen atmosphere, and thus the $(NH_4)_2IrCl_6$ applied on the surface of the glass powder was oxidized to iridium oxide, thereby forming a high-temperature sinterable mixture of iridium oxide/glass fine powder or iridium metal/iridium oxide/glass fine powder.

Example 3

Preparation of Composite pH Sensing Material

The high-temperature sinterable mixture of iridium oxide/glass fine powder or iridium metal/iridium oxide/glass fine powder, formed in Example 2, was molded, and then the molded mixture was sintered at a temperature of 700° C. for 4 hours, thereby preparing a surface renewable iridium oxide/glass composite pH sensing material or a renewable iridium metal/iridium oxide/glass composite pH sensing material.

Example 4

Evaluation of Sensitivity of Electrode

The sensitivity of the electrode using the iridium oxide/glass composite hydrogen ion sensor prepared in Example 3 was measured.

A pH glass electrode and the iridium oxide/glass hydrogen ion electrode were immersed into 0.1 M of a universal buffer solution including phosphoric acid, boron acid, acetic acid and potassium chloride, and the pH of the solution was set to 1. Subsequently, the potentials of the iridium oxide/glass hydrogen ion electrode vs. Ag/AgCl (3.0 M KCl) electrode were measured while changing the pH of the solution in the range of 1 to 13 by adding potassium hydroxide and nitric acid to the solution, and the results thereof are shown in FIG. 2.

In this case, the pH of the solution was increased stepwise to 13, and was then decreased to 1 by adding nitric acid to the solution.

Figure 2:
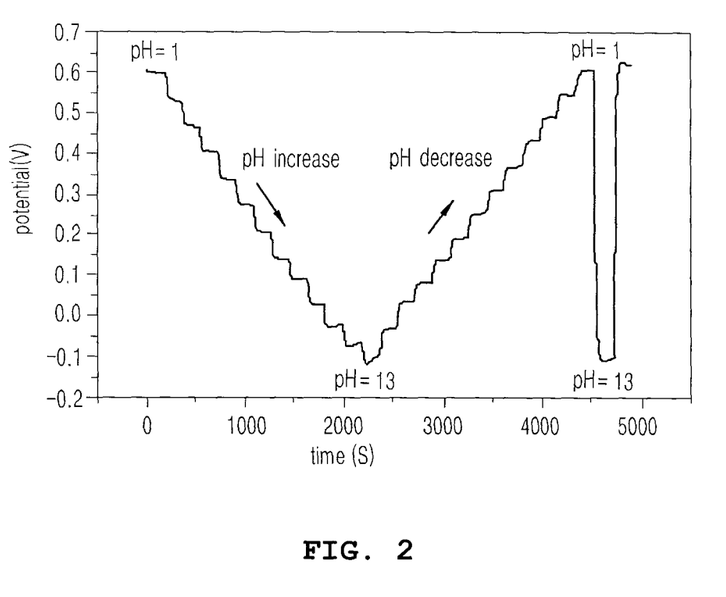
FIG. 2 is a graph showing the potential change of an iridium oxide composite electrode of the present invention to pH change (reference electrode: Ag/AgCl)

As shown in FIG. 2, it can be seen that the potentials of the electrode stabilized at new potentials rapidly depending on the change in the pH of the solution.

Figure 3:
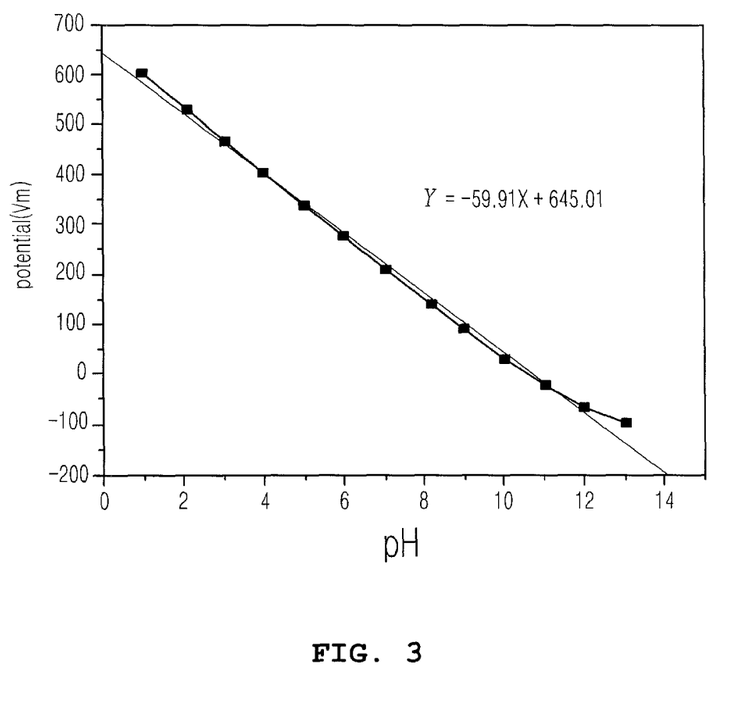
FIG. 3 is a graph showing the electrode potential dependency of an iridium oxide composite electrode of the present invention to pH change.

Meanwhile, the potential of the electrode depending on the pH of the solution is shown in FIG. 3.

As shown in FIG. 3, it can be seen that the iridium oxide/glass hydrogen ion electrode of the present invention exhibits a slope of 59.9 mV/pH unit, and the slope approximates to a theoretical value of 59.2 mV/pH unit.

Example 5

Evaluation of Responsivity of Electrode

Figure 4:
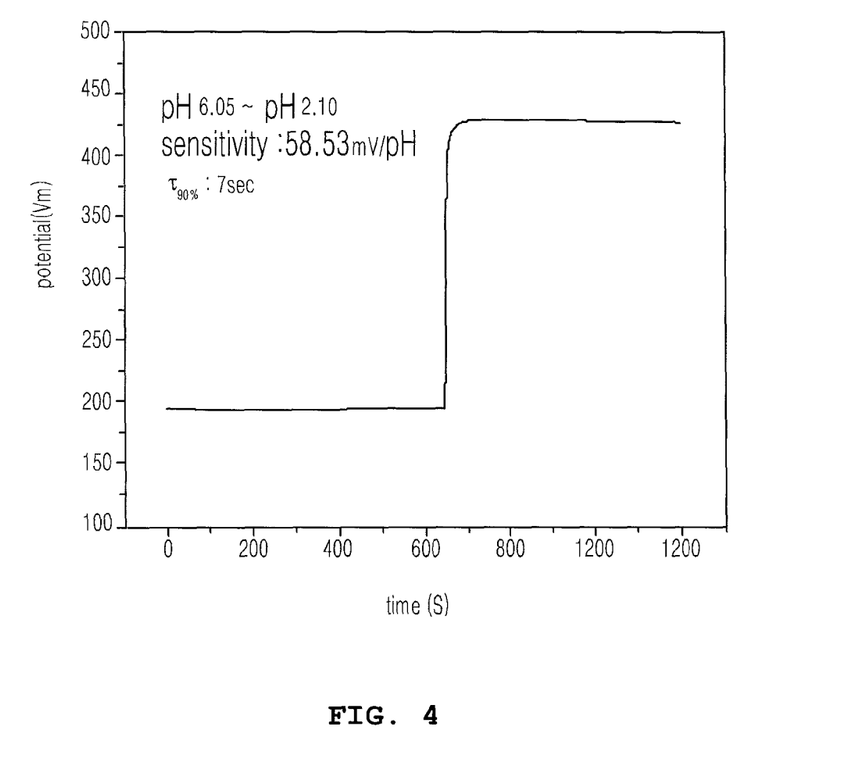
FIG. 4 is a graph showing the response time of an iridium oxide composite pH electrode of the present invention to pH change.

In order to evaluate the response time of the electrode using iridium oxide/glass hydrogen ion electrode prepared in Example 3, the time that it takes for the potential of the electrode to reach 90% of the final potential of the electrode, was measured while the pH of the solution was changed, and the results thereof were shown in FIG. 4.

As shown in FIG. 4, it can be seen that, when the pH of the solution was changed from 6.05 to 2.10, the time $T_{90}$ that it took for the potential of the electrode to reach 90% of the final potential was 7 seconds or less, and thus the electrode exhibits high responsivity.

Example 6

Evaluation of surface renewability of electrode

The surface of the electrode (containing 13% of iridium oxide) prepared in Example 3 was finely grinded using a 2000 grit SiC paper, and then the potential of the electrode was measured in solutions of pH 4, 7, and 10. The response slope was evaluated for seven trials. Between each set of measurements the surface of the electrode was re-grinded completely. Thereafter, the pH sensitivity of the electrode was measured in each case (referring to FIG. 5).

Figure 5:
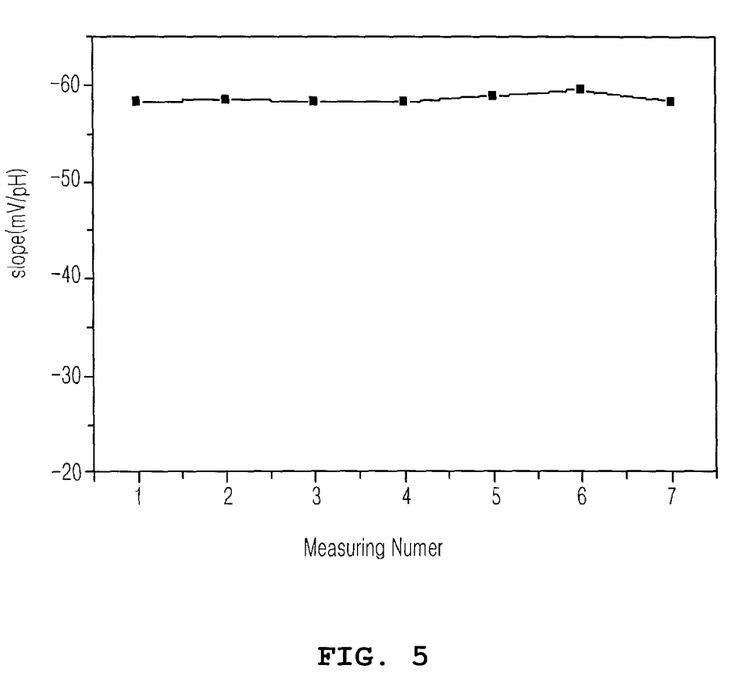
FIG. 5 is a graph showing the hydrogen ion sensing slope depending on the grinding of the surface of an iridium oxide composite pH electrode of the present invention.

As shown in FIG. 5, it can be seen that the average response of the pH sensitivity of the electrode is −58.6 mV/pH unit, and the relative standard deviation (rsd) thereof is 0.76%, which is excellent.

Example 7

Evaluation of Stability of Electrode

Figure 6:
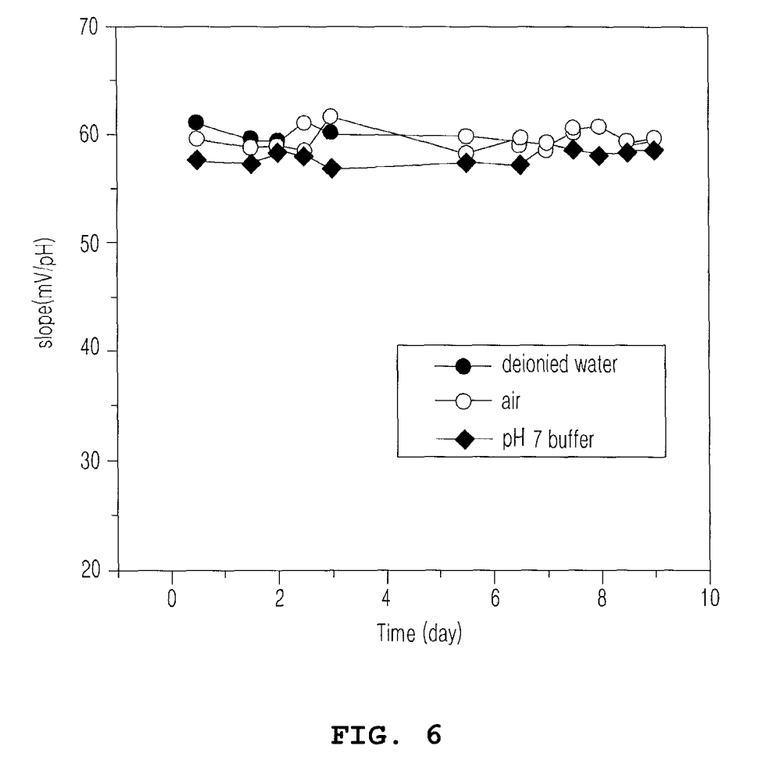
FIG. 6 is a graph showing the long-term stability of an iridium oxide composite electrode of the present invention in various storage conditions.
Figure 7:
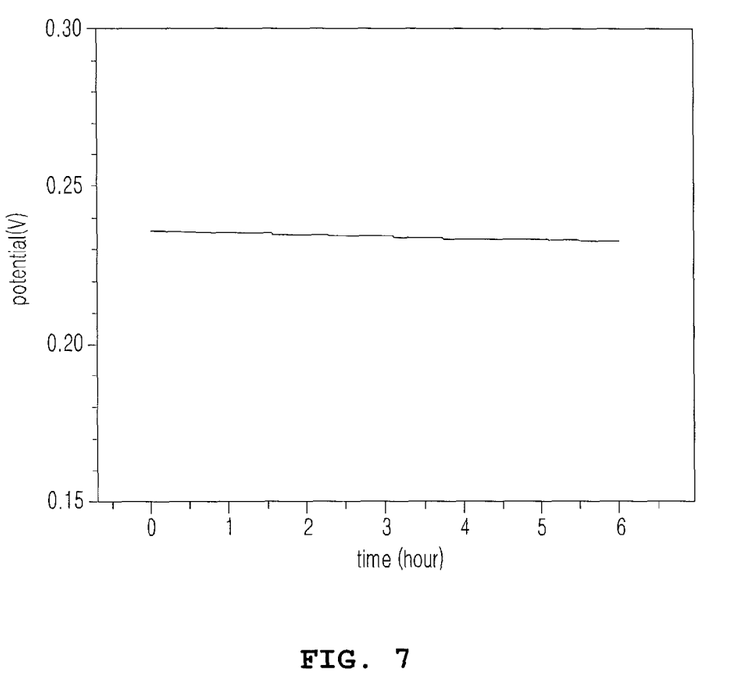
FIG. 7 is a graph showing the potential stability of an iridium oxide composite electrode of the present invention.

FIGS. 6 and 7 show the changes in the responsivity of iridium oxide composite pH electrode depending on the length of the period of use thereof.

FIG. 6 shows the response slope of the electrode to hydrogen ion concentration when the solution is neutral (pH 7), that is, when the electrode is left in air or is stored in distilled water or a neutral buffer solution for a long time.

In FIG. 6, it can be seen that the deviation in the responsivity of the electrode was 1 mV/pH unit, which is very small.

In FIG. 7, it can be seen that 3 mV of electrode voltage drift is exhibited as the result of measuring electrode voltage for 6 hours.

As described above, a iridium oxide/glass hydrogen ion electrode according to the present invention is effective in that the electrode has very high physical strength because it has a glass or ceramic medium, unlike conventional electrodes, and, when the electrode is contaminated or inactivated, the surface of the electrode can be regenerated through a simple grinding process because iridium oxide, which is a sensing material, is uniformly included in the entire electrode medium.

Accordingly, the iridium oxide/glass hydrogen ion electrode according to the present invention can be usefully used in a water-quality monitoring system for monitoring the hydrogen ion concentration of a solution for a long period, an online measurement system, and pH measurement for samples causing serious contamination on the surface of sensor.

What is claimed is:

1. A hydrogen ion electrode comprising:
   a metal wire; and
   a hydrogen ion sensor connected to the metal wire, wherein:
   the hydrogen ion sensor has a shape of a pellet which has such a length to allow the hydrogen ion sensor to be renewed by grinding a surface of the hydrogen ion sensor, the hydrogen ion sensor having a first end connected to the metal wire and a second end exposed to an exterior, the hydrogen ion sensor extending in a lengthwise direction from the first end to the second end; and
   the hydrogen ion sensor is formed of a sintered mixture of iridium oxide and glass or a sintered mixture of iridium oxide and ceramic material,
   wherein the hydrogen ion sensor is formed by the steps, including:
   a step of dispersing sinterable glass fine powder, ceramic powder or ceramic precursor powder in a solution containing iridium compound, evaporating and drying a solvent from the solution, thus applying the iridium compound on the surface of glass fine powder, ceramic powder or ceramic precursor powder, and then pyrolyzing compounds applied at below sintering temperature, thereby forming a sinterable mixture of iridium oxide and glass fine powder or a sinterable mixture of iridium oxide and ceramic material; and
   a further step of sintering the sinterable mixture into a hydrogen ion sensor pellet, thereby forming the sintered mixture of iridium oxide and glass or the sintered mixture of iridium oxide and ceramic material,
   wherein the hydrogen ion sensor further includes inactive conductive material, and the hydrogen ion sensor is formed of a sintered mixture of inactive conductive material, iridium oxide and glass,
   wherein:
   the inactive conductive material is coated on a surface of sinterable glass; then
   the sinterable glass coated with the inactive conductive material, is dispersed in the solution which contains iridium compound, a solvent is evaporated and dried from the solution, the iridium compound is applied on the surface of the glass, and then the compounds applied are pyrolyzed at below the sintering temperature, thereby forming a sinterable mixture of inactive conductive material, iridium oxide and glass; and then
   the sinterable mixture of inactive conductive material, iridium oxide and glass, is sintered into a hydrogen ion sensor pellet, thereby forming the sintered mixture of inactive conductive material, iridium oxide and glass.

2. The electrode according to claim 1, wherein the hydrogen ion sensor having the shape of the pellet has a length of 0.5 mm or more.

3. The electrode according to claim 1, further comprising a connection part connecting the metal wire and the hydrogen ion sensor.

4. The electrode according to claim 3, wherein the connection part is made of silver epoxy.

5. The electrode according to claim 3, further comprising a protector surrounding the hydrogen sensor and the connection part, and a body surrounding the metal wire.

6. The electrode according to claim 5, wherein the protector is made of epoxy or plastic, and the body is made of glass or plastic.

7. The electrode according to claim 1, wherein the inactive conductive material is selected from the group consisting of platinum (Pt), iridium (Ir), palladium (Pd), and gold (Au).

8. The electrode according to claim 1, wherein the inactive conductive material is formed using a pyrolysis reduction method, a simple mixing method, or an electroless plating method.

* * * * *